(12) United States Patent
Willey et al.

(10) Patent No.: US 9,675,989 B2
(45) Date of Patent: Jun. 13, 2017

(54) STRUCTURE MODIFYING APPARATUS

(71) Applicant: The Procter & Gamble Company, Cincinnati, OH (US)

(72) Inventors: Alan David Willey, Cincinnati, OH (US); Jacob Robert Adams, Cincinnati, OH (US); Earl Osborne, Cincinnati, OH (US); Daniel E Machenheimer, Union, KY (US); Vanessa Marie Melendez, Cincinnati, OH (US); Randall Alan Watson, Loveland, OH (US); Philip Andrew Sawin, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 173 days.

(21) Appl. No.: 14/479,427

(22) Filed: Sep. 8, 2014

(65) Prior Publication Data
US 2016/0067734 A1 Mar. 10, 2016

(51) Int. Cl.
*B05C 9/12* (2006.01)
*B05D 3/06* (2006.01)
(Continued)

(52) U.S. Cl.
CPC ............... *B05C 9/12* (2013.01); *A45D 2/00* (2013.01); *A45D 34/04* (2013.01); *A46B 9/021* (2013.01); *A46B 9/023* (2013.01); *A46B 11/00* (2013.01); *A46B 11/0062* (2013.01); *A46B 15/0034* (2013.01); *A46B 15/0036* (2013.01); *A61N 5/0617* (2013.01); *B05C 17/03* (2013.01); *B05C 21/00* (2013.01); *B05D 3/06* (2013.01); *B05D 3/12* (2013.01); *D06F 87/00* (2013.01); *A45D 2200/205* (2013.01); *A46B 2200/104* (2013.01);
(Continued)

(58) Field of Classification Search
CPC combination set(s) only.
See application file for complete search history.

(56) References Cited

U.S. PATENT DOCUMENTS 4,014,605 A * 3/1977 Fletcher ............... B65H 5/021
226/94
5,556,468 A * 9/1996 Legrain .............. A45D 26/0014
118/202

(Continued)

FOREIGN PATENT DOCUMENTS

DE 102013202122 A1 6/2014
WO WO 01/88076 11/2001
WO WO 2006/130647 A1 12/2006

OTHER PUBLICATIONS

International Search Report and Written Opinion dated Dec. 9, 2015, U.S. Appl. No. 14/479,427, 11 pgs.
(Continued)

*Primary Examiner* — David Walczak
(74) *Attorney, Agent, or Firm* — David K Mattheis

(57) ABSTRACT

An apparatus for activating a chemistry disposed upon a target structure includes a handle; a structure contacting element rotatably attached to the handle and adapted to roll without slipping upon a target structure; and a radiant energy source having an emissive outlet at least partially within the structure contacting element wherein said contacting element is at least partly transparent or translucent to said radiant energy.

18 Claims, 2 Drawing Sheets

(51) Int. Cl.
  *A46B 11/00* (2006.01)
  *A45D 34/04* (2006.01)
  *B05C 21/00* (2006.01)
  *B05D 3/12* (2006.01)
  *B05C 17/03* (2006.01)
  *A45D 2/00* (2006.01)
  *A61N 5/06* (2006.01)
  *D06F 87/00* (2006.01)
  *A46B 9/02* (2006.01)
  *A46B 15/00* (2006.01)

(52) U.S. Cl.
  CPC .............. *A46B 2200/1053* (2013.01); *A61N 2005/0644* (2013.01)

(56) References Cited

U.S. PATENT DOCUMENTS

| | | | |
|---|---|---|---|
| 5,939,060 | A | 8/1999 | Cappel et al. |
| 6,369,025 | B1 | 4/2002 | Back et al. |
| 6,492,322 | B1 | 12/2002 | Baker et al. |
| 6,573,233 | B1 | 6/2003 | Altmann et al. |
| 6,787,510 | B2 | 9/2004 | Dahlinger et al. |
| 7,125,416 | B2 | 10/2006 | Kent |
| 7,135,451 | B2 | 11/2006 | Brown et al. |
| 7,563,757 | B2 | 7/2009 | Detroch et al. |
| 7,605,116 | B2 | 10/2009 | Brooker et al. |
| 8,017,108 | B2 | 9/2011 | Baker et al. |
| 8,177,332 | B2 * | 5/2012 | Thompson ............. B41J 11/002 347/101 |
| 8,591,133 | B2 * | 11/2013 | Ho ...................... A45D 34/041 401/209 |
| 2004/0147984 | A1 | 7/2004 | Altshuler et al. |
| 2007/0185553 | A1 | 8/2007 | Kennedy |
| 2007/0198004 | A1 | 8/2007 | Altshuler et al. |
| 2008/0014011 | A1 | 1/2008 | Rossen |
| 2008/0262394 | A1 | 10/2008 | Pryor et al. |
| 2009/0038083 | A1 | 2/2009 | Barnabas et al. |
| 2009/0061004 | A1 | 3/2009 | Birkel et al. |
| 2009/0299236 | A1 | 12/2009 | Pryor et al. |
| 2011/0040235 | A1 | 2/2011 | Castel |
| 2011/0123958 | A1 | 5/2011 | Piergallini et al. |
| 2012/0109041 | A1 | 5/2012 | Munz |
| 2012/0114585 | A1 | 5/2012 | Dempsey et al. |
| 2012/0207532 | A1 | 8/2012 | Ho |
| 2012/0209151 | A1 | 8/2012 | Zhou et al. |
| 2012/0215292 | A1 | 8/2012 | Gustavsson |
| 2012/0324653 | A1 | 12/2012 | Chawla et al. |
| 2013/0065811 | A1 | 3/2013 | Broeckx et al. |
| 2013/0068849 | A1 | 3/2013 | Birkel et al. |
| 2013/0080279 | A1 | 3/2013 | Daily et al. |
| 2013/0184693 | A1 | 7/2013 | Neev |
| 2013/0218066 | A1 | 8/2013 | Duquet et al. |
| 2013/0344454 | A1 | 12/2013 | Nath |
| 2015/0327653 | A1 | 11/2015 | Decaux et al. |
| 2016/0067669 | A1 | 3/2016 | Willey et al. |

OTHER PUBLICATIONS

International Search Report and Written Opinion dated Dec. 8, 2015, U.S. Appl. No. 14/479,434, 12 pgs.

U.S. Appl. No. 14/479,434, filed Sep. 8, 2014, Alan David Willey et al.

* cited by examiner

STRUCTURE MODIFYING APPARATUS

FIELD OF THE INVENTION

The invention relates to apparatus for modifying a prepared target structure via electromagnetic and mechanical interactions. The invention relates particularly to the modification via an electromagnetic activation of a chemical modifier applied to a target structure while concurrently applying a mechanical force to the structure.

BACKGROUND OF THE INVENTION

Chemical compositions adapted to interact with and modify the mechanical properties of fibers and fibrous structures have been described. Such compositions may be used to alter the appearance of a fibrous structure and/or change the mechanical properties of the fibers and the overall structure. The composition may be applied to the surface of the fibers/structures and subsequently activated by exposure to electromagnetic radiation of appropriate wavelength and intensity. This exposure activates the composition. Upon activation, the composition alters the mechanical properties of the fibers and structure via the altered fibers. This alteration may be achieved, at least in part, through covalent binding of an element within the composition to the fibers/structure being modified.

One form of said alteration is the retention of the fibers and structure of the form present at the time of activation. A straight fiber and flat structure may retain this shape after the exposure to the radiation and a wrinkled and/or otherwise curved or formed structure may retain its wrinkled and/or otherwise curved or formed state. What is desired is an apparatus adapted to concurrently impart a desired mechanical state to a structure and to appropriately irradiate the structure to activate a composition applied to the structure in anticipation of the use of the apparatus.

SUMMARY OF THE INVENTION

In one aspect, an apparatus for activating a chemistry disposed upon a target structure includes a handle; a structure contacting element rotatably attached to the handle and adapted to roll without slipping upon a target structure; and a radiant energy source having an emissive outlet at least partially within the structure contacting element wherein said contacting element is at least partly transparent or translucent to said radiant energy.

DETAILED DESCRIPTION OF THE INVENTION

Figure 1:
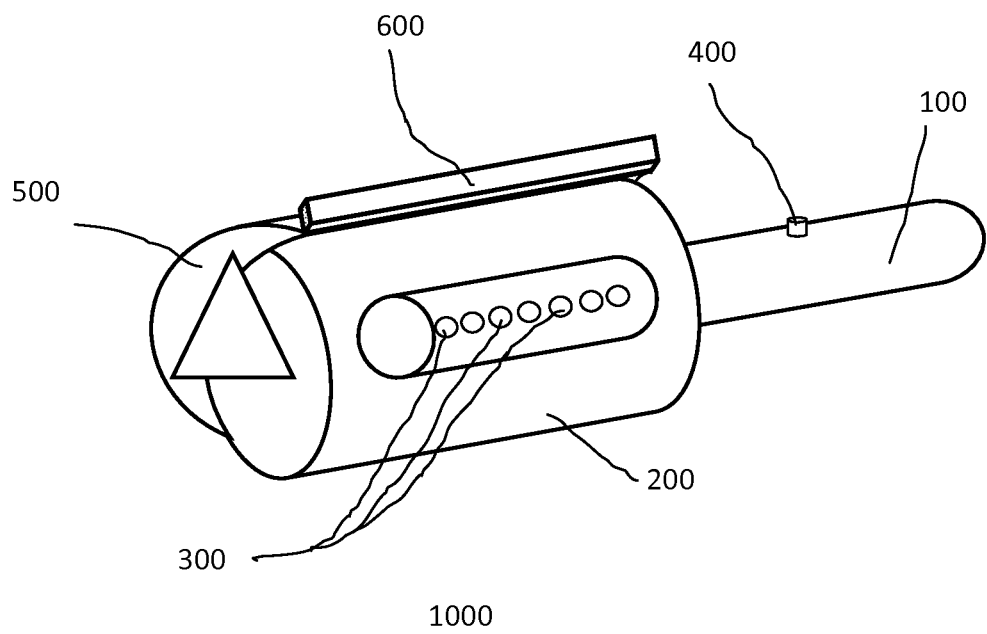
FIG. 1 provides a schematic perspective illustration of an embodiment of the invention.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

An apparatus comprises a source of electromagnetic radiation and an element adapted to interact mechanically with a target structure. The apparatus further includes a handle to enable the user of the apparatus to grip it and to apply force against the target structure through the structure contacting surface.

The source of electromagnetic radiation may be provided as a resistive incandescent source, a semi-conductor based light emitting diode (LED) source, a source wherein the emissions originate from heating an element through the combustion of a fuel composition, a LASER source, arc lamp or any other electromagnetic sources as are known in the art. In one aspect the electromagnetic radiation may be of a wavelength generally considered to be within the visible range of the electromagnetic spectrum (e.g. between about 400 and about 700 nm). In another aspect the electromagnetic radiation may be of a wavelength generally considered to be within the ultraviolet range of the electromagnetic spectrum (e.g. between about 100 nm and about 400 nm). In another aspect the electromagnetic radiation may be of a wavelength generally considered to be within the infrared range of the electromagnetic spectrum (e.g. between about 700 nm and about 1000 nm).

In a further aspect, the emissive spectrum of the source may be tailored to include only those wavelengths which most efficiently interact with any of the chemical components of the composition applied to the target surface. The source may be provided such that the emissive spectrum broadly includes such wavelengths or such that the emissive spectrum narrowly includes such wavelengths or such that the emissive spectrum comprises a monochromatic radiation output. In one embodiment, the source may emit a spectrum of wavelengths which effectively interact with an intermediate composition resulting in the subsequent emission of radiation by the intermediate composition. This emitted radiation subsequently interacts with any of the chemical components of the composition, such as a photoactive component. Non-limiting examples of photoactive components may include photo-acids, photo-bases, photo-active electron-transfer agents, photo-active energy transfer agents, and the like.

The radiant energy source may be disposed within the structure contacting element such that the radiation emitted from the source has a direct transmission path to the structure contacting element. Alternately, the radiant energy source may be disposed adjacent the structure contacting element such that the radiation emitted from the source has a direct transmission path to the surface being treated so that the radiation impinges on the surface, generally, concurrent with the structure contacting element.

Alternatively, the source may be disposed outside the structure contacting element and the emitted radiation transmitted via a wave guide, fiber optic conduit or other means to a point of subsequent emission within the structure contacting element.

In one embodiment, the source may comprise an array of illumination elements such as LEDs disposed in a regular arrangement on the external surface of a handle of the apparatus and within a curved outer shell which is at least partially transparent to the radiation emitted by the LEDs. The LEDs may be narrow spectrum or broad spectrum in the output. They may be substantially similar in output across the respective elements of the array or may comprise a collection of distinctly different output spectra across the array elements. In one embodiment, the LED source has an emission spectrum comprised substantially of radiation at a wavelength of between about 100 nm and about 400 nm, (UV), In one embodiment, the source may have a spectrum of between about 400 nm and about 700 nm, (visible). In one embodiment, the source may have a spectrum of between about 700 nm and about 1000 nm, (infrared).

Alternatively, the structure contacting element may comprise the intermediate composition described above. In such an embodiment, the emissions of the source interact with the intermediate composition leading to a subsequent emission by the composition. At least a portion of the structure contacting element may be transparent to at least a portion of this subsequent transmission spectrum such that the target structure will be irradiated by that portion of the spectrum.

The source may be considered as including a power element adapted to support the radiative emissions. Exemplary power elements include: portable energy storage elements such as batteries, wired connection to a power grid such as 120 VAC household power via a wall outlet and a wired plug, capacitor or other forms of stored energy, solar cell, chemical energy cell, piezo-electric cell, combustion of a flammable fluid such as methane, propane, or butane, or other forms of energy transfer capable of interacting with a radiation source to yield electromagnetic radiation.

The apparatus further comprises a switching element adapted to control the provision of power to the radiation source. Exemplary switching elements include: rocker switches, membrane switches, slider switches, rotating switches, and other switching elements as are known in the art. In another embodiment the switching element may include automated switching features. In one aspect the automated switching feature may comprise a time-based switching features that actuates the provision of power to the radiation source as a function of duration of exposure and/or that actuates the provision of power to the radiation source after a given length of time and/or that actuates pulses of power to the radiation source including a duration of the power and/or a duration of lapses between instance of provision of power to the radiation source. In another embodiment the automated switching feature may comprise a feedback element that actuates the provision of power to the radiation source as a function of another stimulus of the apparatus. In one aspect the feedback element may actuate the provision of power to the radiation source as a function of pressure applied to the contacting element as indicated by a load cell incorporated within the apparatus, thereby providing an automatic on/off feature as a function of use of the apparatus. In another aspect the feedback element may actuate the provision of power to the radiation source as a function of pressure applied to the handle as indicated by a load cell incorporated within the apparatus thereby providing an automatic on/off feature as a function of the apparatus being held or released by the user.

In another aspect the operation of the apparatus may be triggered by the rotation of the structure contacting element. The structure contacting element may be of any shape or form appropriate to the application of the desired mechanical shaping of the target surface. In one aspect said mechanical shaping may include flattening/smoothing/de-wrinkling of said target surface such as the smoothing/de-wrinkling of a fabric. In another aspect said mechanical shaping may include curling/forming said target surface such as the curling of the hair. The structure contacting element may or may not completely enclose the radiation source. In one aspect the structure contacting element is a sphere. In one aspect the structure contacting element is a cylinder. In another aspect the structure contacting element is conical or frustoconical.

The structure contacting element may be configured to roll without slipping upon the surface of the targeted structure. Rolling without slipping enables the element to impart a force upon the target that is normal to the structure as it is in contact with the element and does not result in forces upon the structure due to the contacting element being dragged along the surface and the attendant stress in the target structure due to such dragging of the contacting element. Similarly, rolling without slipping enables the element to curl the target surface (e.g. the hair) more easily.

The configuration of the structure contacting element to roll without slipping represents an ideal scenario and in actual practice, the configured element may slip to some extent as it is moved across a target surface or structure.

The rolling of the contacting element may be facilitated by supporting a cylindrical contacting element with rolling element bearings on an axis substantially similar to, if not identical with, the axis of the cylindrical contacting element. A single bearing element may be utilized and the contacting element cantilevered from that bearing element or a pair of bearing elements may be utilized with one element at each end of the cylindrical contacting element to distribute the load applied to the element at each end of the cylinder.

At least a portion of the structure contacting element may be transparent to at least a portion of the emissive spectrum of the source. This construction facilitates the exposure of the contacted structure to the transmitted portion of the spectrum. This exposure enables the apparatus to activate chemicals which have been disposed upon the surface. Exemplary materials for the fabrication of the transparent portion of the contacting element include glass and polymers selected according to their transmission characteristics with regard to the desired transmission spectrum. Portions of the emitted spectrum may be more desirable for transmission to the surface according to the activation characteristics of the deposited target chemistry.

The outer surface of the structure contacting element may comprise a smooth surface or alternatively, a surface having a regular or irregular structure developed upon it. In use, the target structure may conform to the shape of the outer surface of the structure contacting element as the disposed chemical composition is activated thereby imparting the shape of the contacting surface to the target structure via activation of the deposited chemistry.

The outer surface of the structure contacting element may be configured so as to have a particular coefficient of friction relative to the surface being treated. In one aspect, the outer surface of the structure contacting element may have a low coefficient of friction (COF) relative to the surface being treated to facilitate the gliding of the structure contacting element over the surface. Without being bound by theory it is believed that a low COF may be preferable when smoothing/de-wrinkling a surface. In another aspect, the outer surface of the structure contacting element may have a high coefficient of friction (COF) relative to the surface being treated to facilitate the gripping of the structure contacting element to the surface. Without being bound by theory it is believed that a high COF may be preferable when curling/forming a surface such as the curling of the hair.

In one aspect the material comprising the structure contact element may have the coefficient of friction appropriate to the desired function of the apparatus. Exemplary Coefficients of Friction include values greater than about 0.1, as well as values less than about 1.5, as determined according to ASTM 3702. In another aspect, the surface of the structure contact element may be modified so as to have the desired coefficient of friction. In one embodiment, said modification of said structure contact element may be achieved by surface-coating the structure contact element with a lubricant or adhesive.

In another aspect, the desired coefficient of friction between the structure contact element and the target surface may be further influenced by the composition. In one embodiment, lubricants may be added to the chemical composition to reduce the coefficient of friction between the structure contact element and the target surface. In another embodiment, materials with adhesive properties may be added to the chemical composition to increase the coefficient of friction between the structure contact element and the target surface.

The apparatus may further comprise a cover element disposed to partially occlude the outer surface of the rolling element. The occlusion by the cover effectively shields a user of the apparatus from the emissions while continuing to enable the exposure of the target structure to these emissions. The cover may comprise an inner surface which reflects all or at least a portion of the emissions of the apparatus thereby raising the flux level to which the target structure is exposed during a use of the apparatus.

The apparatus may further comprise a chemical composition dispensing system. In the broadest terms, this system may comprise a composition reservoir, a dispersion element, and a trigger mechanism enabling the flow of the composition from the reservoir to and out of the dispersion element. The dispersion element may comprise one or more outlets disposed such that the composition will be dispersed upon the target structure in advance of an exposure of the structure to the emissions of the apparatus.

In practice, a user may apply a treatment composition to a structure prior to or concurrent with the application of a force via the apparatus. The dispensing system of the apparatus may be used for this purpose or a separate dispensing element may be utilized for the purpose of providing the treatment composition. The apparatus may be provided for use as a kit including the apparatus itself together with one or more treatment compositions and possibly including a separate treatment composition dispensing/application element.

As provided in FIG. 1, an embodiment of the apparatus 1000, comprises a handle 100 coupled to a structure contacting element 200, an array of radiant energy sources 300 disposed within the structure contacting element, a switch 400, a cover 500, and a dispensing element 600.

Figure 2:
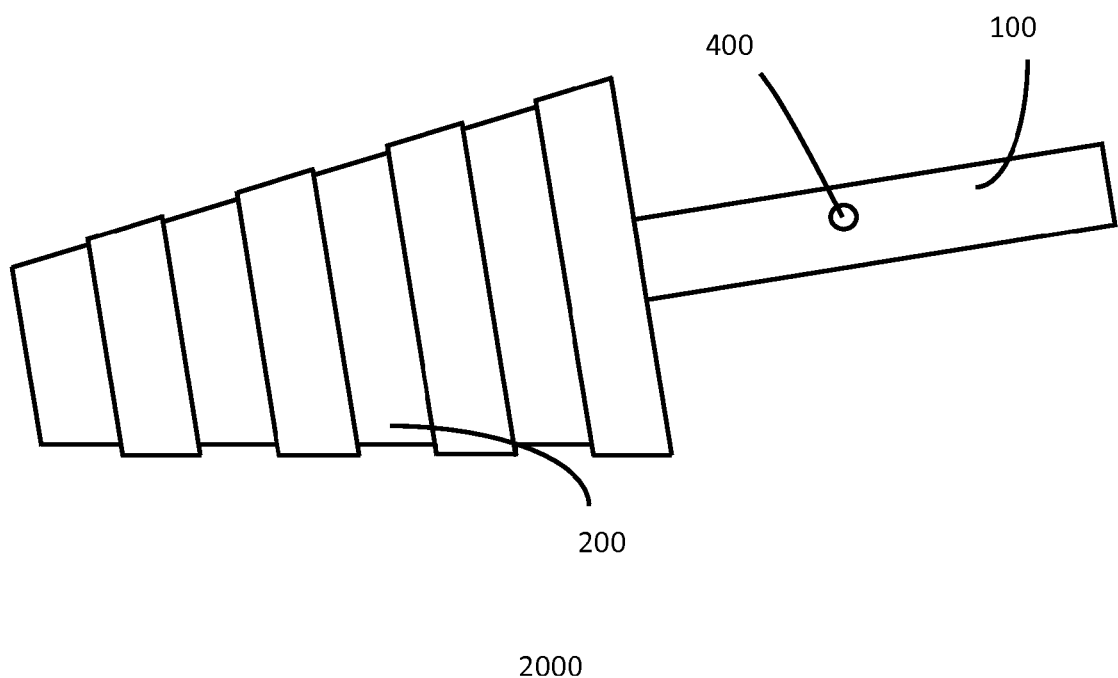
FIG. 2 provides a schematic side view illustration of an embodiment of the invention.

As provided in FIG. 2, an apparatus 2000 comprises a handle 100 coupled to a frustoconical structure contacting element 200 having a three dimensional pattern upon its structure contacting surface, and a switch 400.

Treatment Composition

The treatment composition of the present invention comprises an active agent and a photocatalyst. The treatment composition optionally further comprises a carrier. For purposes of the present invention, treatment compositions encompass concentrated compositions for subsequent dilution before use, as well as diluted compositions that are ready for use.

Active Agent

The active agent of the present invention may comprise a thiol. Thiols generally include organic species bearing at least one sulfur atom as part of at least one functional group. Thiols may be mono-thiols bearing one functional group comprising at least one sulfur atom, dithiols bearing two functional groups comprising at least one sulfur atom, or polythiols bearing more than two functional groups comprising at least one sulfur atom. Further, thiols may be primary thiols bearing sulfhydryl-groups, in which the sulfur atom bears one hydrogen atom and one organic moiety (Group 1), thiol-ethers bearing sulfide-groups in which the sulfur atom bears two organic moieties (Group 2), disulfides in which the sulfur atom is bonded to another sulfur atom (Group 3), sulfoxides bearing sunfinyl-groups in which the sulfur atom further includes a double bond to an oxygen atom (Group 4), sulfones bearing sulfonyl-groups in which the sulfur atom further includes two double bonds to oxygen atoms (Group 5), sulfinic acids bearing sulfino-groups in which the sulfur atom further includes a double bond to an oxygen atom and a hydroxyl-group (Group 6), sulfonic acids bearing sulfo-groups in which the sulfur atom further includes two double bonds to oxygen atoms and a hydroxyl-group (Group 7), thiones bearing carbonothioyl-groups in which the sulfur atom further includes a double bond to a carbon atom (Group 8) or thials in which the sulfur atom further includes a double bond to a carbon atom which further comprises a hydrogen atom (Group 9), as reflected in the table below:

| Group 1 | R—SH |
| Group 2 | R—S—R |
| Group 3 | R—S—S—R |
| Group 4 | R—S(=O)—R |
| Group 5 |  |
| Group 6 | R—S(=O)—OH |
| Group 7 |  |
| Group 8 | R—C(=S)—R |
| Group 9 | R—C(=S)—H |

In the above table, R is independently selected from the group consisting of $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ hydroxy, $C_1$-$C_{32}$ alkoxy, $C_1$-$C_{32}$ substituted alkoxy, $C_1$-$C_{32}$ alkylamino, and $C_1$-$C_{32}$ substituted alkylamino.

The active agent of the present invention may comprise a high-polarity functional group, preferably selected from the group consisting of hydroxyl groups, carboxylic acid groups, and combinations thereof. It is believed that these high polarity functional groups, to the extent that they comprise a substantial portion of the active molecule, negatively impact the effectiveness of the active material due to the extensive hydrogen-bonding capability of these high-polarity groups. As such, the active agent of the present invention comprising a high-polarity functional group preferably include one or more of the following limitations regarding the portion of the active material that may comprise said high-polarity functional groups.

The active agent of the present invention may comprise a non-acid carbonyl or an equivalent of non-acid carbonyl. Non-acid carbonyls generally include organic species bearing at least one carbonyl group as part of at a functional group wherein that functional group is not a carboxylic acid. It is believed that higher polarity of carboxylic acid moieties limits diffusion into the fibrous material especially at pH in which the acid is in its conjugate base form and carries a positive charge. Non-acid carbonyls as described herein are less polar and do not carry a formal charge at any pH. It is believed that non-acid carbonyls penetrate the fibrous material more readily relative to the non-acid carbonyls. Non-limiting examples of non-acid carbonyl functional groups include ketones, esters, aldehydes, amides, acyl halides, and carbonates. Equivalents of non-acid carbonyls include acetals, hemiacetals, ketals, and hemiketals.

The active agent of the present invention mat comprise a sugar. Sugars are useful because they are naturally-derived, which can be preferred by consumers versus synthetic compounds. This is not only for perceived health and sensitivity reasons, but also for sustainability and environmental reasons—sugars break down naturally and quickly and do not require special disposal methods. Furthermore, sugars are also easy to source and relatively inexpensive.

The active agent of the present invention may comprise a monoamine, diamine, or polyamine Amines generally include an organic species bearing at least one nitrogen atom as part of a functional group. Amines may be monoamines bearing one functional group comprising at least one nitrogen atom, diamines bearing two functional groups each comprising at least one nitrogen atom, or polyamines bearing more than two functional groups each comprising at least one nitrogen atom.

The active agent herein has a molecular weight of below about 1000 g/mol, below about 750 g/mol, below about 500 g/mol, below about 300 g/mol, from about 50 g/mol to about 250 g/mol, or from about 80 g/mol to about 150 g/mol. It is believed that the relatively low molecular weight of the active agent facilitates penetration of the active agent into the fiber structure of the fibrous material, thereby allowing the fibrous material to be shaped by the method of the present invention.

The treatment composition of the present invention preferably comprises from about 0.1% to about 99.99%, from about 0.1% to about 40%, from about 0.1% to about 15%, from about 1% to about 10%, or from about 2% to about 7%, by weight of the treatment composition, of active agent.
Photocatalyst The photocatalyst may be any photoacid or photobase (or conjugate thereof) having a pKa (or pKb) value that decreases (or increases) upon exposure to electromagnetic radiation. The electromagnetic radiation may be of any suitable wavelength to result in the respective decrease or increase in pKa or pKb, and preferably is in the range of from about 300 nm to about 750 nm. For example the electromagnetic radiation may be ambient light, sunlight, incandescent light, fluorescent light, LED light, laser light, solar light, and the like. The electromagnetic radiation may fall within any classification along the electromagnetic spectrum, but preferably is visible light. It will be readily apparent to one of ordinary skill in the art that the appropriate wavelength or wavelengths of light will be dependent upon the identities of the one or more photocatalysts employed.

In addition, the suitable light may be provided from any source capable of illuminating the fibrous material. For example, ambient sunlight, incandescent light, fluorescent light, and the like may provide electromagnetic radiation of suitable wavelength. Accordingly, the electromagnetic radiation may be provided by conventional sources such as lamps and portable or battery-powered lights. In addition, specific devices may be developed or adapted for use with the compositions and method described herein. For example, a hair brush configured to incorporate LEDs that provide light of a suitable wavelength may be used.

In various embodiments, the photocatalyst is a photoacid such as, for example, a hydroxylated aromatic compound (i.e. a hydroxyl-substituted aromatic compound), a sulfonated pyrene compound, an onium salt, a diazomethane derivative, a bissulfone derivative, a disulfuno derivative, a nitrobenzyl sulfonate derivate, a sulfonic acid ester derivative, a sulfonic acid ester of an N-hydroxyimide, or combinations thereof. The photoacid is preferably a hydroxyl-substituted aromatic compound.

Photoacid catalysts may include, for example, hydroxy-substituted aromatics such as, for example, 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-bromo-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, pelargonidin, or mixtures thereof.

Photoacid catalysts may include onium salts such as, for example, bis(4-tert-butylphenyl)iodonium perfluoro-1-butanesulfonate, diphenyliodonium perfluoro-1-butanesulfonate, diphenyliodonium-9,10-dimethoxyanthracene-2-sulfonate, diphenyliodonium hexafluorophosphate, diphenyliodonium nitrate, diphenyliodonium p-toluenesulfonate, diphenyliodonium triflate, (4-methylphenyl)diphenylsulfonium triflate, (4-methylthiophenyl)methyl phenyl sulfonium triflate, 2-naphthyl diphenylsulfonium triflate, (4-phenoxyphenyl)diphenylsulfonium triflate, (4-phenylthiophenyl)diphenylsulfonium triflate, thiobis(triphenyl sulfonium hexafluorophosphate), triarylsulfonium hexafluoroantimonate, triarylsulfonium hexafluorophosphate salt, triphenylsulfonium perfluoro-1-butanesulfonate, triphenylsulfonium triflate, tris(4-tert-butylphenyl)sulfonium perfluoro-1-butanesulfonate, tris(4-tert-butylphenyl)sulfonium triflate, bis(4-tert-butylphenyl)iodonium p-toluenesulfonate, bis(4-tert-butylphenyl)iodonium triflate, (4-bromophenyl) diphenylsulfonium triflate, (tert-butoxycarbonylmethoxynaphthyl)diphenylsulfonium triflate, (tert-butoxycarbonylmethoxyphenyl)diphenylsulfonium triflate, (4-tert-butylphenyl)diphenylsulfonium triflate, (4-chlorophenyl) diphenylsulfonium triflate, (4-fluorophenyl) diphenylsulfonium triflate, [4-[2-hydroxytetradecyl)oxy]phenyl]phenyliodonium hexafluoroantimonate, (4-iodophenyl)diphenylsulfonium triflate, (4-methoxyphenyl)diphenylsulfonium triflate, diphenyliodo hexafluorophosphate, diphenyliodo hexafluoroarsenate, diphenyliodo hexafluoroantimonate, diphenyl p-methoxyphenyl triflate, diphenyl p-toluenyl triflate, diphenyl p-isobutylphenyl triflate, diphenyl p-t-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthyl sulfonium triflate, diphenyliodonium trifluoromethanesulfonate, (p-tert-butoxyphenyl) phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethyl-sulfonium trifluoromethanesulfonate, trimethylsulfonium p-toluenesulfonate, cyclohexylmethyl(2-oxocyclohexyl)-sulfonium trifluoromethanesulfonate, cyclohexylmethyl(2oxocyclohexyl) sulfonium p-toluenesulfonate, dimethylphenyl-sulfonium trifluoromethanesulfonate, dimethylphenyl-sulfonium p-toluenesulfonate, dicyclohexylphenylsulfonium trifluoromethanesulfonate, dicyclohexylphenylsulfonium p-toluenesulfonate, trinaphthylsulfonium trifluoromethane-sulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis-[methyl(2-oxocyclopentyl)sulfonium trifluoromethane-sulfonate], 1,2'-naphthylcarbonylmethyltetrahydrothiophenium triflate, or mixtures thereof.

Photoacid catalysts may include diazomethane derivatives such as, for example, bis(benzenesulfonyl)-diazomethane, bis(p-toluenesulfonyl)diazomethane, bis(xylenesulfonyl)diazomethane, bis(cyclohexylsulfonyl)-diazomethane, bis(cyclopentylsulfonyl) diazomethane, bis(n-butylsulfonyl) diazomethane, bis(isobutylsulfonyl)-diazomethane, bis(sec-butylsulfonyl)diazomethane, bis(n-propylsulfonyl) diazomethane, bis(isopropylsulfonyl)-diazomethane, bis(tert-butylsulfonyl) diazomethane, bis(n-amylsulfonyl) diazomethane, bis(isoamylsulfonyl)-diazomethane, bis(sec-amylsulfonyl)diazomethane, bis(tert-amylsulfonyl)diazomethane, 1-cyclohexylsulfonyl-1-(tert-butylsulfonyl) diazomethane, 1-cyclohexylsulfonyl-1-(tert-amylsulfonyl) diazomethane, 1-tert-amylsulfonyl-1-(tert-butylsulfonyl)diazomethane, or mixtures thereof.

Photoacid catalysts may include glyoxime derivatives such as, for example, bis-o-(p-toluene-sulfonyl)-α-dimethylglyoxime, bis-o-(p-toluenesulfonyl)-α-diphenylglyoxime, bis-o-(p-toluenesulfonyl)-α-dicyclohexyl-glyoxime, bis-o-(p-toluenesulfonyl)-2,3-pentanedioneglyoxime, bis-o-(p-toluenesulfonyl)-2-methyl-3,4-pentane-dioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butane-sulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethyl-glyoxime, bis-o-(camphorsulfonyl)-α-dimethylglyoxime, or mixtures thereof.

Photoacid catalysts may include bissulfone derivatives such as, for example, bisnaphthylsulfonylmethane, bistrifluoromethylsulfonylmethane, Bismethylsulfonylmethane, bisethylsulfonylmethane, bispropylsulfonylmethane, bisisopropylsulfonylmethane, bis-p-toluenesulfonylmethane, bisbenzenesulfonylmethane, 2-cyclohexyl-carbonyl-2-(p-toluenesulfonyl)propane (β-ketosulfone derivative), 2-isopropyl-carbonyl-2-(p-toluenesulfonyl) propane (β-ketosulfone derivative), or mixtures thereof.

Photoacid catalysts may include disulfono derivatives such as, for example, diphenyl disulfone, dicyclohexyl disulfone, or mixtures thereof.

Photoacid catalysts may include nitrobenzyl sulfonate derivatives such as, for example, 2,6-dinitrobenzyl p-toluenesulfonate, 2,4-dinitrobenzyl p-toluenesulfonate, or mixtures thereof.

Photoacid catalysts may include sulfonic acid ester derivatives such as, for example, 1,2,3-tris(methanesulfonyloxy) benzene, 1,2,3-tris(trifluoro-methanesulfonyloxy)benzene, 1,2,3-tris(p-toluenesulfonyloxy)benzene, or mixtures thereof.

Photoacid catalysts may include sulfonic acid esters of N-hydroxyimides such as, for example, N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethyl-benzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethane-sulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, N-hydroxy-5-norbornene-2,3-dicarboxyimide p-toluenesulfonate, N-hydroxynaphthalimide triflate, N-hydroxy-5-norbornene-2,3-dicarboximide perfluoro-1-butanesulfonate, or mixtures thereof.

Photoacid catalysts may also include fluoresceins and derivatives thereof; preferably halogen substituted fluoresceins; more preferably bromo- and iodo-fluoresceins such as dibromo fluorescein, diodo fluorescein, rose bengal, erythrosine, eosin (e.g. Eosin Y);

Hydroxy flavones and derivatives thereof; preferably hydroxyl flavones, dihydroxy flavones, trihydroxy flavones, tetrahydroxy flavones; more preferably 3-hydroxy flavones, 7-hydroxy flavones, 5,7-hydroxy flavones, 4',5,7-trihydroxy flavone, and quercitin;

Hydroxyl triarylmethanes, preferably FD&C Green 3;

Anthocyanidins and anthocyanins; preferably cyanidin, malvidin, palargonidin and extracts containing anthocyanins such as elderberry, blueberry, cranberry, bilberry, red cabbage, sorghums, blackberry, black current, cherry red and black raspberry.

In some aspects, the photocatalyst is 8-hydroxyquinoline, which may act as a photoacid catalyst in lower pH solutions or as a photobase catalyst in higher pH solutions. In other aspects, the photocatalyst is 8-hydroxy-1,3,6-pyrentrisulfonic acid trisodium salt (D&C Green 8).

In some aspects, the photocatalyst is a photobase. Photobase catalysts may include derivatives of trityl alcohols such as, for example, Malachite green. Photobase catalysts may also include acridine derivatives such as, for example, 9-hydroxy-10-methyl-9-phenyl-9,10-dihydroacridine. Photobase catalysts may also include photoactive carbamate-containing compounds.

The photocatalyst may be present in the compositions and methods described herein in an amount from about 0.00050% to 30%, from about 0.01% to about 15%, from about 0.01% to about 10%, or from about 0.01% to about 5%, by weight of the treatment composition. Generally, there is a preferred concentration of the photocatalyst. The preferred concentration of photocatalyst depends, in part, on a variety of factors including, for example, the chemical structure of the catalyst, the reaction medium, the reaction type, the type of fibrous material, and whether the treatment composition is diluted before/during use in the methods of the present invention.

Carrier

The compositions described herein optionally, and preferably, further comprise a carrier suitable for carrying, dispersing or dissolving the active agent, the photocatalyst, and any other components to facilitate making the treatment composition and/or application of the treatment composition onto the fibrous material. The carrier may comprise one or more of a solvent, an emulsifier, a surfactant, or other dispersant. The carrier may also be a physiologically-acceptable carrier. The properties of a suitable carrier are dependant, at least in part, on the properties of the other components of the composition and the substrate to be modified.

A suitable carrier operates to disperse or dissolve the active material, the photocatalyst, and any other components, and to facilitate application of the composition onto the substrate surface. A suitable carrier facilitates sufficient contact between the active material and the substrate. In various embodiments, a physiologically-acceptable carrier may be any carrier, solvent, or solvent-containing composition that is suitable for application to physiological tissues such as human hair and human skin, for example, in the context of personal care products. In various embodiments, a physiologically-acceptable carrier is a cosmetically- or dermatologically-acceptable carrier.

A suitable carrier may be a solvent. In personal and household care product applications, for example, water is a useful solvent. In various embodiments, the compositions described herein may include water in an amount from 1% to 98% by weight relative to the total weight of the composition. Water is also a physiologically acceptable carrier. Additional solvent or solvent-containing physiologically-acceptable carriers include, but are not limited to, hydroxyl-containing liquids (e.g., alcohols), silicones, oils, hydrocarbons, glycols, and combinations thereof. In certain embodiments, for example, where the active material is at least partially insoluble in water, other solvents, dispersants, or emulsifiers may be used as physiologically-acceptable carriers, alone or in combination with each other and/or with water.

Alcohols, such as ethanol, can be useful carriers, especially for assisting in solubilizing the active agent and/or photocatalyst.

A suitable carrier is therefore generally used to dilute and/or emulsify the components forming the compositions described herein. A suitable carrier may dissolve a component (true solution or micellar solution) or a component may be dispersed throughout the carrier (suspension, dispersion or emulsion). The carrier of suspension, dispersion or emulsion may be the continuous phase thereof, in which other components of the suspension, dispersion or emulsion are distributed on a molecular level or as discrete or agglomerated particles throughout the carrier. The preparation of such emulsions or dispersions of the active in these cases may be highly important. Small particles contribute to an intimate contact between the active, the substrate and the photoacid catalyst, increasing the reaction rate.

It will be readily apparent to one of ordinary skill in the art that the appropriate carrier(s) are dependent upon the specific active agent(s), photocatalyst(s), and other optional component(s) used in the compositions described herein.

Optional Components

The treatment compositions and methods described herein may optionally include a variety of components, which will depend on the nature of the treatment composition. The treatment composition is preferably a consumer product composition, more preferably a personal care product composition or a household care composition. For example, in various aspects, the treatment compositions and methods described herein may include surfactants, emulsifiers, oxidants, reductants, pH regulators, emollients, humectants, proteins, peptides, amino acids, additive polymers, glossers, oils and/or fatty acids, lubricants, sequestrants/chelators, antistatic agents, rheology modifiers, feel agents, fillers, dyes, preservatives, perfumes, other functional components, or combinations thereof. Particular optional components may be found in the CTFA International Cosmetic Ingredient Dictionary, Tenth Edition, 2004; and in McCutcheon, Detergents and Emulsifiers, North American Edition (1986). It will be readily apparent to one of ordinary skill in the art that the particular optional components utilized will be dependant, at least in part, upon the specific applications for the compositions and methods.

Non-limiting examples of treatment compositions, in which the active agent and photocatalyst can be incorporated, include:

liquid laundry detergents, such as those described in detail in US 2012/0324653 A1;

granular laundry detergents, such as those described in detail in U.S. Pat. No. 7,605,116;

unit dose laundry detergents, such as those described in detail in WO 2013/039964 A1, WO 2006/057905 A1, WO 2006/130647 A1;

liquid fabric softeners, such as those described in detail in U.S. Pat. Nos. 7,135,451, 6,369,025 and 6,492,322;

dryer-added fabric softener sheets, such as those described in detail in U.S. Pat. No. 6,787,510;

fabric treatment sprays, such as those described in detail in U.S. Pat. No. 5,939,060, WO 01/88076, US 2009/0038083 A1, and U.S. Pat. No. 6,573,233;

hair shampoos, such as those described in detail in US 2013/0080279 A1;

hair conditioners, such as those described in detail in U.S. Pat. No. 8,017,108;

hair styling compositions, such as those described in detail in US 2009/0061004 and EP2570192;

cosmetics, including mascara compositions, such as those described in detail in US 2012/0114585.

The treatment compositions of the present invention can be in the form of a liquid composition or a solid composition (preferably a water-soluble solid composition). If in the form of a liquid composition, the liquid composition is preferably packaged in an opaque package, and/or a package which blocks electromagnetic radiation at a wavelength which activates the photocatalyst of the treatment composition (which does not necessarily have to be an opaque package), to prevent the premature photoactivation of the treatment composition. Solid compositions can be preferred as solid compositions tend not to prematurely photoactivate until contacting aqueous solutions. Solid compositions are also preferably packaged in opaque packages to further prevent premature photoactivation. If in the form of a solid composition, the solid composition is preferably dissolved in a carrier, such as water, before being applied to the fibrous material.

In at least one aspect, the treatment composition is substantially free of, or completely free of, formaldehyde, derivatives of formaldehyde, methylene glycol, formalin, and any compound that produces formaldehyde upon heating. "Heating" means raising the temperature of the compound above 25° C. In at least one aspect, the treatment composition is substantially free of, or completely free of, a quaternary ammonium compound and/or a surfactant. In at least one aspect, the treatment composition is substantially free of, or completely free of, a ceramide compound, an alpha-hydroxy acid, a thioglycolate and/or thiolactate compound, a bisulfate compound, clay, and/or a reducing agent. In at least one aspect, the treatment composition is substantially free of, or completely free of, a carbonate compound.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for activating a composition disposed upon a target structure, the apparatus comprising: a handle, a structure contacting element rotatably attached to the handle and adapted to roll upon a target structure, and a radiant energy source having an emissive outlet adjacent said structure contacting element, wherein the radiant energy source is at least partially enclosed by the structure contacting element, wherein the structure contacting element comprises a composition which emits radiation upon exposure to radiation from the radiant energy source.

2. The apparatus according to claim 1 wherein the radiant energy source is fixedly attached to the handle.

3. The apparatus according to claim 1 wherein the radiant energy source comprises a plurality of emissive sources.

4. The apparatus according to claim 1 wherein the structure contacting element is transparent to at least a portion of a radiation spectrum emitted by the radiant energy source.

5. The apparatus according to claim 1 further comprising a cover disposed around a portion of the structure contacting element and occluding that portion of the element.

6. The apparatus according to claim 1 further comprising a chemical composition reservoir and a composition dispensing element fluidly connected to the reservoir.

7. The apparatus according to claim 1 wherein the structure contacting element comprises a substantially smooth structure contacting surface.

8. The apparatus according to claim 1 wherein the structure contacting element comprises a structure contacting surface having a three-dimensional pattern.

9. The apparatus according to claim 1 wherein the coefficient of friction of the structure contacting element is less than 1.5.

10. The apparatus according to claim 1 wherein the coefficient of friction of the structure contacting element is greater than 0.1.

11. The apparatus according to claim 1 wherein the structure contacting element further comprises a surface coating.

12. The apparatus according to claim 11 wherein said surface coating decreases the coefficient of friction between the structure contacting element and the target surface.

13. The apparatus according to claim 11 wherein said surface coating increases the coefficient of friction between the structure contacting element and the target surface.

14. The apparatus according to claim 1 wherein an emission spectrum of the radiant energy source consists substantially of radiation having a wavelength of between about 100 nm and about 400 nm.

15. The apparatus according to claim 1 wherein an emission spectrum of the radiant energy source consists substantially of radiation having a wavelength of between about 400 nm and about 700 nm.

16. The apparatus according to claim 1 wherein an emission spectrum of the radiant energy source consists substantially of radiation having a wavelength of between about 700 nm and about 1000 nm.

17. The apparatus according to claim 1 wherein the structure contacting element comprises a cylinder.

18. The apparatus according to claim 1 wherein the structure contacting element is frustoconical.

\* \* \* \* \*